United States Patent
Lampropoulos et al.

[11] Patent Number: 6,050,981
[45] Date of Patent: Apr. 18, 2000

[54] WOUND IRRIGATION SYSTEM WITH FLEXIBLE SHIELD

[75] Inventors: Fred P. Lampropoulos, Sandy; Brent E. Mabey, Salt Lake City; Arlin Dale Nelson; Gregory R. McArthur, both of Sandy; Jerrold L. Foote, Salt Lake City, all of Utah

[73] Assignee: Merit Medical Systems, Inc., South Jordan, Utah

[21] Appl. No.: 09/075,660

[22] Filed: May 11, 1998

[51] Int. Cl.⁷ .................................................... A61M 5/00
[52] U.S. Cl. .......................... 604/289; 128/849; 128/919
[58] Field of Search ..................................... 604/289, 290, 604/310, 311, 192, 263, 187, 110; 433/80, 116, 166; D24/130; 128/846, 847, 849–856, 917, 919

[56] References Cited

U.S. PATENT DOCUMENTS

| | | | |
|---|---|---|---|
| D. 344,133 | 2/1994 | Stamler | D24/130 |
| 4,573,975 | 3/1986 | Frist et al. | 604/192 |
| 4,692,140 | 9/1987 | Olson | 604/40 |
| 4,769,003 | 9/1988 | Stamler | 604/39 |
| 4,857,060 | 8/1989 | Rosenberg | 604/192 |
| 4,898,588 | 2/1990 | Roberts | 604/187 |
| 4,976,254 | 12/1990 | Dash et al. | 128/4 |
| 5,067,899 | 11/1991 | Paschal | 433/116 |
| 5,224,940 | 7/1993 | Dann et al. | 604/290 |
| 5,248,307 | 9/1993 | Sokoloff | 604/317 |
| 5,275,559 | 1/1994 | Rihel | 433/116 |
| 5,376,003 | 12/1994 | Rizkalla | 433/116 |
| 5,483,973 | 1/1996 | Benson et al. | 128/760 |
| 5,496,288 | 3/1996 | Sweeney | 604/263 |
| 5,496,290 | 3/1996 | Ackerman | 604/268 |
| 5,522,403 | 6/1996 | Bark et al. | 128/849 |
| 5,527,297 | 6/1996 | Paul | 604/263 |
| 5,609,163 | 3/1997 | Beard | 128/846 |
| 5,735,833 | 4/1998 | Olson | 604/289 |

*Primary Examiner*—Ronald K. Stright, Jr.
*Assistant Examiner*—David J. Cho
*Attorney, Agent, or Firm*—Workman, Nydegger & Seeley

[57] ABSTRACT

The present invention relates to a system for irrigating a wound with wound irrigation fluid and for preventing substantial splashback of the wound irrigation fluid. The system comprises: (i) fluid delivery device for delivering wound irrigation fluid; and (ii) a flexible wound irrigation shield configured such that the shield prevents substantial splashback of the irrigation fluid upon irrigation of a wound. The shield is configured to be disposed, preferably removably, on the fluid delivery device. The flexible shield is substantially conformable to a desired wound area, enabling the practitioner to irrigate awkward, uneven, and hard to reach areas. The shield can be folded into a compact position, then opened into a larger shield. The fluid delivery device comprises (i) a fluid source for providing wound irrigation fluid; and (ii) an adaptor for transmitting fluid from the fluid source to the wound. In one embodiment, the adaptor has a substantially planar face that is substantially coplanar with the plane defined by the shield, thereby preventing patient puncture. The preferred adaptor, preferably a multi-part adaptor, features spray pattern adjustability, removable coupling to the shield, the capacity for removably coupling to a variety of different fluid sources, and a variety of other features and advantages.

22 Claims, 9 Drawing Sheets

WOUND IRRIGATION SYSTEM WITH FLEXIBLE SHIELD

BACKGROUND OF THE INVENTION

1. The Field of the Invention

This invention is in the field of medical instruments. More specifically, this invention is in the field of irrigation systems with splash back prevention shields.

2. The Relevant Technology

Irrigators are commonly used in medical and dental applications to clean wounds before dressing the wounds. Lacerations are commonly surrounded by contaminants including debris and fluids which are desirably removed before dressing the wound.

Certain irrigator systems include irrigation shields designed to prevent discharged fluid from splashing back upon the practitioner during irrigation of a wound. Such irrigation shields are designed to protect the practitioner against the splashback of fluids delivered by the practitioner as well as splashback of infectious materials and fluids which surround the wound. For example, the shields are designed to prevent fluids containing pathogens associated with diseases such as Hepatitis B and Acquired Immune Deficiency Syndrome (AIDS) from being splashed back upon the practitioner during irrigation.

There are a variety of problems associated with previous designs, however, including the fact that irrigating shields are typically rigid and may often be incompatible with awkward, uneven regions of the body. In addition, the shields previously known in the art are either large and bulky for transport and storage or are too small to cover a desired area appropriately.

As shown in FIG. 4 of U.S. Pat. No. 4,769,003 to Stamler, for example, fluid delivered from the irrigation instrument splashes both inside and outside of the shield. The fluid splashing outside the shield is depicted as splashing broadly away from the shield. Such fluid splashing outside a small shield can splash detrimentally onto the patient, the practitioner, or onto an instrument or fixture within the medical office, potentially contaminating an individual or object. A larger shield, on the other hand, would cover the desired area enough to prevent splash back, but would also be bulky and cumbersome because of its size.

In the past, practitioners have used syringes to irrigate wounds, which allows for the possibility of puncture wounds caused by the syringes. Puncture wounds caused during irrigation are a major concern when using conventional syringes with needles. In addition, the possibility of potential puncture also exists for other irrigators within the art. The wound irrigation splash shield featured in U.S. Pat. No. 5,496,290 to Ackerman, for example, features a tip which, although described as flexible, could damage an eye or ear if placed with too great a force thereon.

There is therefore a need in the art for a wound irrigation shield which is compatible with awkward, uneven regions of the body as well as more flat regions. There is also a need in the art for a wound irrigation shield which is not too large and bulky for transport and storage yet covers a desired area during wound irrigation. There is also a need in the art for wound irrigation shields which do not pose a risk of patient puncture.

SUMMARY AND OBJECTS OF THE INVENTION

It is therefore an object of the invention to provide an improved wound irrigation system.

It is another object of the invention to provide an improved wound irrigation shield.

It is another object of the invention to provide a flexible wound irrigation shield.

It is another object of the invention to provide an irrigation shield which is substantially conformable to a given wound area.

It is another object of the invention to provide a disposable wound irrigation shield.

It is another object of the invention to provide a wound irrigation system which does not injure the patient during use.

It is another object of the invention to provide a wound irrigation system adaptor.

It is another object of the invention to provide an adaptor for delivering fluid from a fluid source to a wound.

It is another object of the invention to provide an adjustable adaptor that can alter a spray pattern as desired.

It is another object of the invention to provide a wound irrigation shield which can be rotated relative to a fluid delivery system.

The present invention relates to a system for irrigating a wound with wound irrigation fluid and for preventing substantial splashback of the wound irrigation fluid. The system comprises: (i) fluid delivery means for delivering wound irrigation fluid; and (ii) a wound irrigation shield configured such that the shield prevents substantial splashback of the irrigation fluid upon irrigation of a wound.

The shield is configured to be disposed on the fluid delivery means and is preferably flexible. The shield is also preferably removable, more preferably disposable. The shield comprises: (i) flexible sheet means for preventing substantial splashback of a fluid applied to a wound; and (ii) hub means for coupling the flexible sheet means to the fluid delivery means. Because of its configuration, the flexible shield is substantially conformable to a given wound area. This enables the practitioner to irrigate virtually any area of the body, including awkward, uneven, and hard to reach areas and other cumbersome bodily regions, without substantial splashback of the contaminating material, irrigation fluids, blood, and the like. Since the shield is preferably flexible, it can be folded into a compact position, then opened into a larger shield. Thus, the shield can both simultaneously prevent splashback over a large area and be stored in a small area. The shield is also preferably lightweight and transparent.

One embodiment of a fluid delivery means for delivering wound irrigation fluid comprises (i) a fluid source for providing wound irrigation fluid; and (ii) means for transmitting fluid from the fluid source to the wound. An example of a preferred transmitting means comprises an adaptor which allows the shield to be retrofitted onto an existing syringe. In one embodiment, the shield comprises a substantially planar shield and the adaptor has a substantially planar face that is substantially coplanar with the plane defined by the shield. This unique configuration prevents inadvertent puncture or irritation by the fluid delivery means.

In addition, the preferred adaptor includes features that allow for adjustments to the spray pattern, removable coupling to the shield, the capacity for removably coupling to a variety of different fluid sources, and a variety of other features and advantages. In one embodiment, the adaptor comprises an adjustable multi-part member, enabling adjustability of the spray pattern of fluid being emitted from an exit hole in the adaptor.

As wound irrigation fluid is delivered to a wound, the irrigation fluid typically intermingles with fluid from the wound such as blood and other bodily fluids. As reference is made throughout this specification and the appended claims to splashback of irrigation fluid, the reference shall be understood as referring to (i) splashback of fluid delivered by the practitioner; (ii) splashback of fluid from the wound; or (iii) splashback of intermingled fluid containing both fluid delivered by the practitioner and fluid from the wound As another major advantage of the invention in one embodiment, the shield snaps onto the fluid delivery means and can be rotated relative to the fluid delivery means. Similarly, the fluid delivery means can be rotated relative to the shield. As a result, it is possible for a practitioner to drape the shield over a given wound area, then rotate the fluid delivery means relative to the shield without substantially moving the shield. Thus, rotation of the fluid delivery means does not substantially move the shield once the shield is disposed on a given area.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention addresses the significant need within the art for a wound irrigation system which can conform to a given wound area. The irrigation system of the present invention covers a desired area during irrigation, yet may be folded compactly for transport and storage in one embodiment. The system also features spray pattern adjustability and greatly reduced risk of patient puncture.

The fluid irrigation system preferably features a flexible, removable, snap-fitting, rotating and disposable irrigation shield. The system also preferably has the capacity for removably employing a variety of different fluid sources, and has a variety of other features and advantages. Certain embodiments of the system will now described in additional detail.

Figure 1:
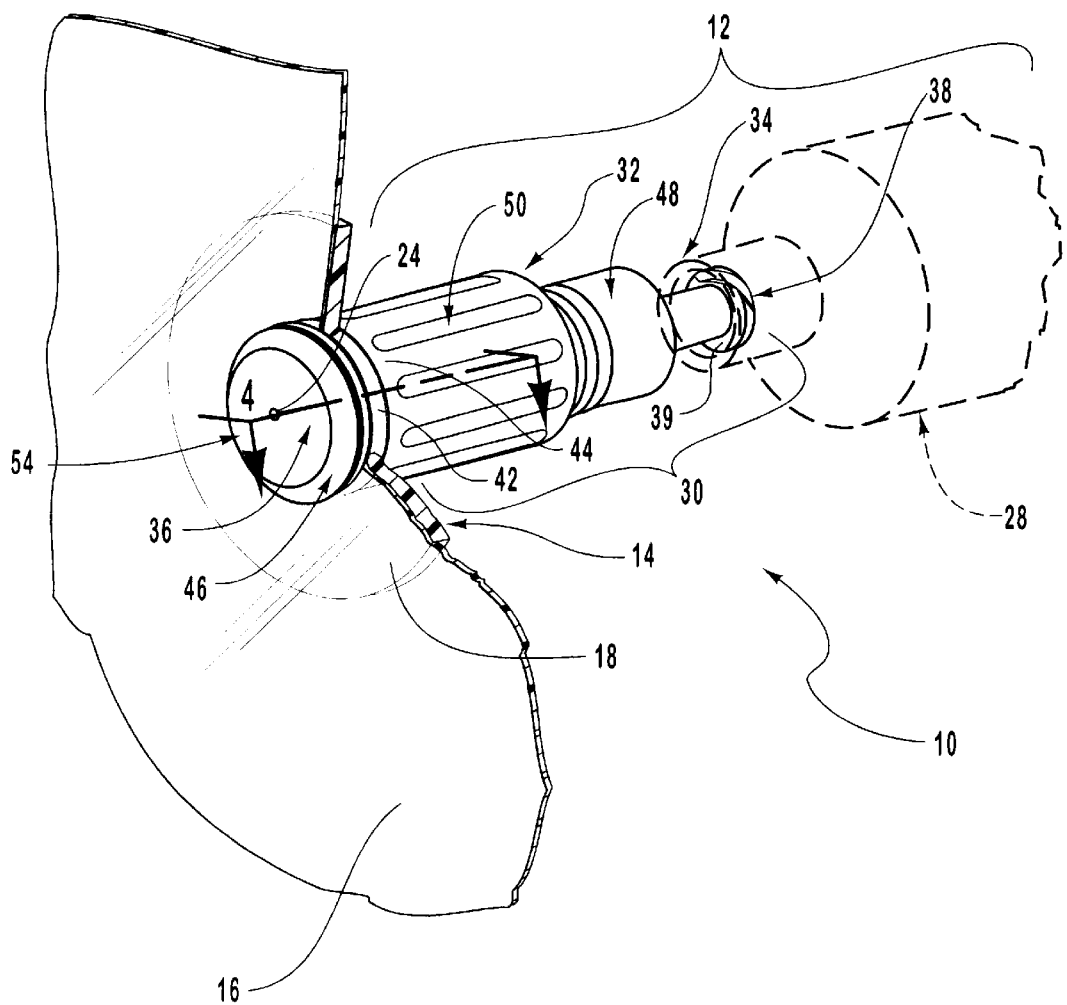
FIG. 1 is a perspective view of a system for irrigating a wound with wound irrigation fluid and for preventing substantial splash back of the wound irrigation fluid. A portion of a fluid source of the system is shown in phantom lines and a wound irrigation shield of the system is shown in a cut-away view.
Figure 2:
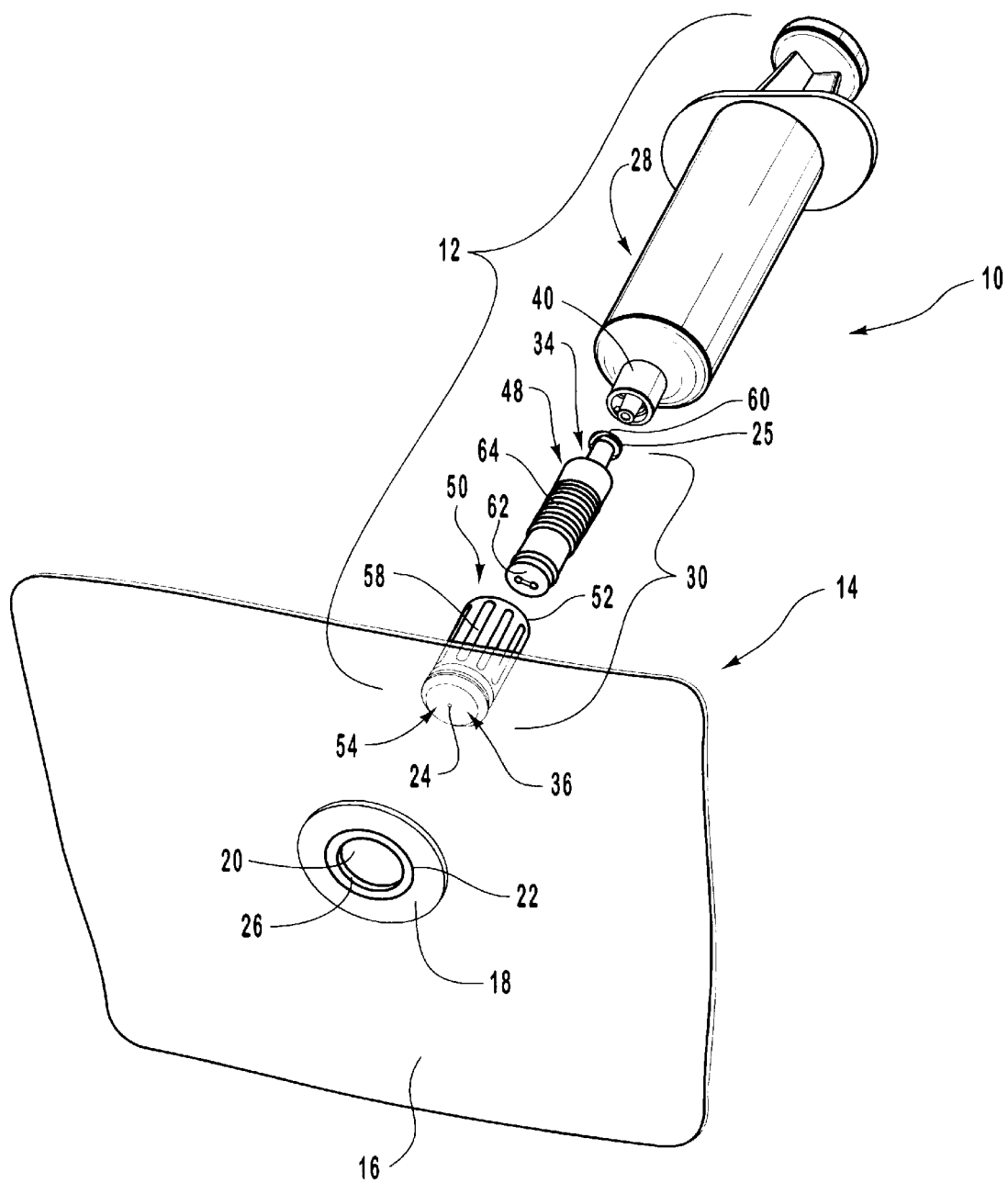
FIG. 2 is an exploded view of the irrigating system shown in FIG. 1.

FIGS. 1 and 2 demonstrate one embodiment of an anti-splashback wound irrigation system 10 of the present invention for irrigating a wound with wound irrigation fluid and for preventing substantial splashback of the wound irrigation fluid. Irrigation system 10 is shown in a partially cutaway, perspective view in FIG. 1 and in an exploded view in FIG. 2.

System 10 comprises: (i) fluid delivery means for delivering wound irrigation fluid, such as a fluid delivery system 12 for applying irrigation fluid to a wound area; and (ii) a flexible wound irrigation shield 14. Shield 14 prevents substantial splashback of irrigation fluid delivered from fluid delivery system 12. Shield 14 is preferably flexible and is conformable to a desired wound area, draping over a particular bodily region to be irrigated. This enables the practitioner to irrigate a variety of different bodily regions, including awkward, uneven, and hard to reach areas and other cumbersome bodily regions without splashback. Since shield 14 is flexible, it can be folded into a compact position, then opened into a larger shield 14. Thus, shield 14 can both simultaneously prevent splashback within a large area and be stored in a small area. Shield 14 is also preferably lightweight, transparent and disposable. Shield 14 couples to fluid delivery system 12 in such a manner that there is no risk of puncture and such that effective splashback-protected irrigation is achieved.

With continued reference to FIGS. 1 and 2, shield 14 comprises (i) flexible sheet means for preventing substantial splashback of a fluid applied to a wound, such as a substantially flexible sheet member 16; and (ii) hub means for coupling the flexible sheet means to the fluid delivery system 12, such as a substantially rigid hub 18.

Substantially flexible sheet member 16 is comprised of a transparent, lightweight conformable plastic material. As used throughout this specification and the appended claims, the term "transparent" is referred to as being clear enough to enable a practitioner to see through the material to thereby view a wound to be irrigated. Sheet member 16 preferably comprises a material which is conformable to a variety of different regions and which readily folds for compact storage, yet covers a large area when desired.

In one embodiment, sheet member 16 is comprised of a biaxial material such that the shield may be folded in any direction. Examples of useful materials for sheet member 16 include polyurethane, polypropylene, polyvinyl chloride, polyvinyl acetate, mixtures and derivatives thereof, or other transparent, flexible plastic materials.

Sheet member 16 is shown in FIG. 2 as having a substantially square configuration. It will be appreciated, however, that sheet member 16 may also have the shape of a circle, rectangle, half-circle, star, diamond or any other of a variety of different shapes depending upon the configuration desired by the user and the intended application. Sheet member 16 is preferably thin and foldable, allowing sheet member 16 to be readily stored.

In a preferred embodiment, sheet member 16 is about 0.001 inches thick to about 0.02 inches thick, more preferably about 0.003 inches thick to about 0.014 inches thick. In a most preferred embodiment, sheet member 16 is about 0.008 inches thick.

Hub 18 is shown in FIGS. 1 and 2 as being a washer-shaped disk having an aperture 20 therethrough defined by an internal rim 22. In the embodiment shown, hub 18 is coupled to sheet member 16 through the use of an adhesive, which is preferably transparent and which connects hub 18 and sheet member 16 in a manner such that the aperture 20 of hub 18 conforms to a similarly situated aperture within sheet member 16.

The substantially rigid hub 18 is durable and prevents bunching or gathering of the flexible sheet member 16 around exit hole 24 of fluid delivery system 12. In a preferred embodiment, hub 18 comprises a transparent, substantially rigid polycarbonate material. However, hub 18 may comprise a variety of different materials, such as a substantially rigid vinyl, polyurethane, polypropylene, polyvinyl chloride, polyvinyl acetate, mixtures and derivatives thereof or other transparent, flexible plastic materials.

Although hub 18 is shown as a separate member that is coupled to sheet member 16, the hub of the shield can readily be integrally coupled to the substantially flexible sheet member of the shield. For example a substantially rigid internal rim 22 of sheet member 16 could readily act as an integrally coupled hub if rim 22 were configured to be permanently or removably coupled to fluid delivery system 12, such as by being sized and configured to snap onto system 12. Thus, in another embodiment, the term "hub" or "hub means" also refers to any portion of the sheet member which permanently or removably couples to the fluid delivery system 12.

Hub 18 enables convenient snapping of hub 18 onto fluid delivery system 12 and removed therefrom. It will also be appreciated that in yet another embodiment, the flexible shield may include a non-integral, flexible, non-rigid hub which is coupled to sheet member 16 through the use of an adhesive, for example.

While hub 18 may be permanently coupled to fluid delivery system 12, hub 18 preferably may be selectively coupled to and decoupled from system 12, enabling disposability and convenience of transport, storage, and manufacture. Since shield 14 is removable and preferably inexpensive to manufacture, it is feasible and possibly more efficient to dispose of shield 14 after each use, rather than attempting to clean and sterilize shield 14 between uses.

The inner diameter 26 of hub 18 serves as a mating surface for removably coupling to fluid delivery system 12. Hub 18 mates with fluid delivery system 12 by being placed thereon or by having system 12 disposed therethrough. Inner diameter portion 26 of hub 18 can be bevelled on one side thereof, or both sides thereof, in order to increase the ease in which hub 18 can be coupled with fluid delivery system 12 and to assist hub 18 in rotating around fluid delivery system 12 when desired.

Hub 18 is shown as being circular in shape, which is preferred because of the resulting range of motion of sheet member 16. However, it will be appreciated that either the outer or inner diameter of hub 18 could also readily be in the shape of a square, rectangle, star, or a variety of different configurations. An inner diameter that is circular allows for freedom of rotation of shield 14 as desired, while other shapes would tend to lock shield 14 in a single position.

Fluid delivery system 12 will now be described in additional detail. In the embodiment shown in FIGS. 1 and 2, fluid delivery system 12 comprises (i) a fluid source 28 for providing wound irrigation fluid; and (ii) means for transmitting fluid from the fluid source 28 to the wound area. A vast number of examples of fluid sources 28 exist, including syringes 28, a squeeze bottle, a fluid bag, a pressurized tank with a valve, a hand pump (see FIG. 8) having a reservoir and means for directing fluid from the reservoir to the means for transmitting fluid, and a variety of other fluid containers, as is known to one skilled in the A wide variety of examples of means for transmitting fluid from the fluid source to the wound area exist, including tubes, pipes, and a variety of other objects or mechanisms having a fluid pathway for transmitting fluid from a fluid source to a wound area. Such tubes, pipes or other objects or mechanisms can be integrally or removably coupled to the desired fluid source. The fluid exit end of a syringe, for example, itself serves as an example of a means for transmitting fluid from a fluid source (e.g., the barrel of the syringe) to a wound area. Shield 14 can be coupled to this exit end of the syringe, for example to form another example of an irrigating system of the present invention.

In the embodiment shown in FIGS. 1 and 2, the means for transmitting fluid from fluid source 28 to the wound comprises an adaptor 30. In the embodiment shown, adaptor 30 comprises: (i) a main body 32 having a fluid entrance end 34, a fluid exit end 36, and a fluid flow conduit 38 providing fluid communication between the fluid entrance end 34 and exit end 36; (ii) means for coupling fluid entrance end 34 to fluid source 28; and (iii) means for coupling fluid exit end 36 to flexible shield 14.

In the embodiment shown in FIGS. 1 and 2, the means for coupling fluid entrance end 34 of main body 32 to fluid source 28 comprises one part of a two-part fastener, such as a female Luer lock component 39 on fluid entrance end 34 of main body 32 which removably couples entrance end 34 to a corresponding male Luer lock component 40 on fluid source 28. It will be appreciated, however, that the fluid entrance end of the adaptor may also be configured with a variety of different parts of a two-part fastener, such as a male Luer lock component which couples to a female component on a fluid source (not shown), a male or female thread which couples to a corresponding female or male thread on the fluid source, a pin which is disposed within a groove on the fluid source (not shown), a groove which receives a pin on the fluid source (not shown), a spring-loaded locking component (not shown), or the entrance end comprising structure configured to be removably coupled to the fluid source in a mating or press fitting relationship (not shown), or any other appropriate coupling means known in the art. In another embodiment (not shown), the means for coupling fluid entrance end 34 to fluid source 28 comprises end 34 and fluid source 28 being permanently coupled, such as by being fused or otherwise fixed together.

Also in the embodiment shown in FIGS. 1 and 2, the means for coupling fluid exit end 36 of main body 32 to flexible shield 14 comprises one part of a two-part fastener, such as exit end 36 of adaptor 30 comprising structure configured to be removably coupled to shield 14 in a mating relationship. In the embodiment shown, the structure configured to selectively mate with shield 14 comprises exit end 36 of adaptor 30 having a groove 42, such as an annular groove, in an exterior surface 44 thereof for removably receiving shield 14.

Adaptor 30 is removably disposed through aperture 20 such that hub 18 mates with groove 42 by snapping into groove 42. Aperture 20 is sized and configured such that hub 18 selectively forms a snap fit engagement within groove 42.

Hub 18 is preferably snap fitted into groove 42 such that the mating relationship between groove 42 and hub 18 allows hub 18 to freely rotate around adaptor 30 (and adaptor rotates within hub 18) without falling off of adaptor 30 and without allowing fluid to seep between hub and adaptor 30 onto the practitioner. Consequently, it is possible for a practitioner to drape shield 14 over a given wound area, then rotate the fluid delivery means within shield 14 without substantially moving shield 14. Thus, rotation of adaptor 30 does not substantially move shield 14 once shield 14 is disposed on a given area.

In another embodiment, the means for coupling the fluid exit end of the main body of the adaptor to an irrigation shield may comprise a variety of different parts of a two-part fastener, such as a male or female thread configured to couple to a female or male thread on the irrigation shield (not shown), a pin which is disposed within a groove on the shield (not shown), a groove which receives a pin on the shield (not shown), a spring-loaded locking component (not shown), the exit end being subject to a press fit arrangement, or any other appropriate coupling means known in the art.

In yet another embodiment, shield 14 may be permanently coupled to exterior surface 44 of exit end 36, such as by being fused thereto. However, the preferred removability of shield 14 fosters disposability of shield 14 and also enables the practitioner to irrigate a wound by holding system 12 behind shield 14 and dispensing fluid through the aperture 20 in shield 14. For convenience of mating hub 18 with groove 42, the distal rim 46 of exterior surface 44 of adaptor 30 can be bevelled to facilitate insertion of adaptor 30 through hub 18.

In the embodiment shown in FIGS. 1 and 2, main body 32 of adaptor 30 comprises a multi-part member, enabling adjustability of the spray pattern of fluid flowing out of the exit hole 24. By adjusting certain parts with respect to each other, the spray pattern can be adjusted. Main body 32 comprises a two-part member. However, the multi-part member may have a variety of different parts, such as two, three, four, five parts, and so on. In another embodiment, the adaptor comprises a one-part member.

Although many different configurations will accomplish the desired spray pattern adjustability, in the embodiment shown, adaptor 30 comprises: (i) a fluid entrance tube 48 coupled to fluid source 28; and (ii) a fluid exit tube 50 having exit hole 24 therein.

Fluid exit tube 50 has a complementary inner surface for receiving entrance tube 48 therein. Entrance tube 48 and exit tube 50 are configured to be concentrically disposed. Fluid entrance tube 48 is selectively adjustable with respect to the longitudinal axis of fluid exit tube 50, thereby enabling the user to selectively adjust the spray pattern of fluid flowing out of the exit hole 24 of fluid exit tube 50.

While fluid exit tube 50 can be configured in a variety of different ways. Tube 50 is shown in FIGS. 1 and 2 as comprising a hollow, cylindrical-shaped member. Exit tube 50 has a proximal opening 52 at one end thereof and a distal face 54 at an opposing exit end 36 thereof. Exit tube 50 is selectively, removably coupled to fluid entrance tube 48, such as by having an internal female threaded portion 56 (see FIG. 4) on the interior surface thereof which couple to corresponding male threads on entrance tube 48.

Figure 4:
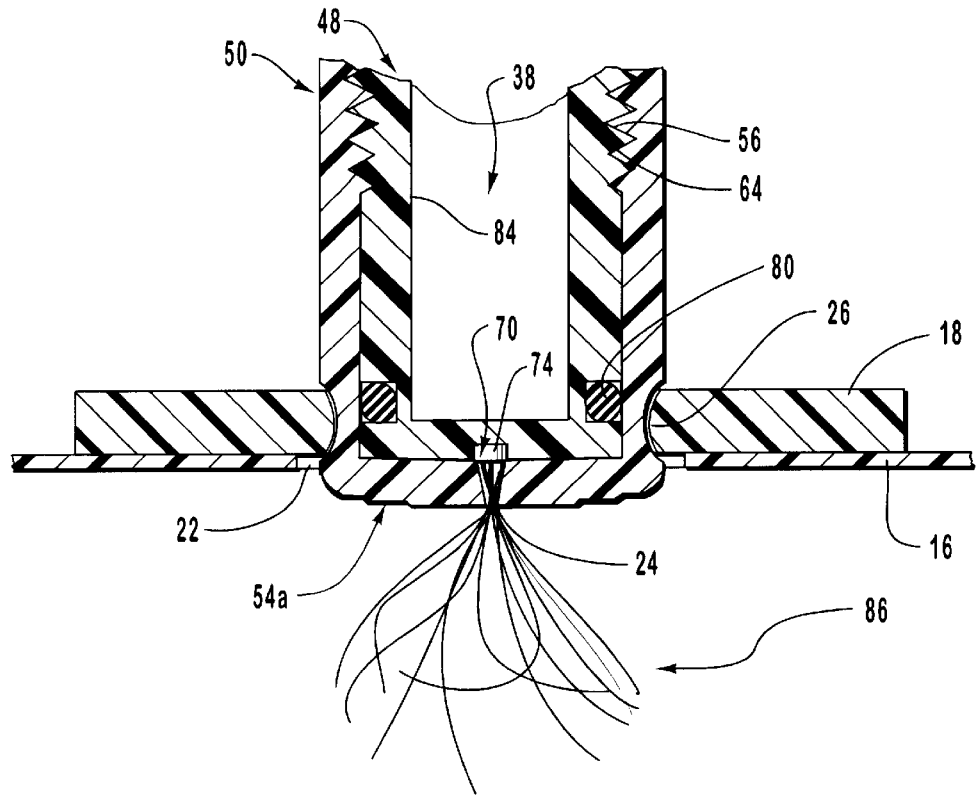
FIG. 4 is a cross-sectional, cut-away view of the irrigating system shown in FIG. 1 with the distal face of the entrance tube disposed against the inner surface of the distal face of an exit tube, which creates a widely diffused mist pattern of fluid flowing from an exit hole. An alternative distal face of the exit tube having a slightly tiered, substantially planar surface is shown.
Figure 5:
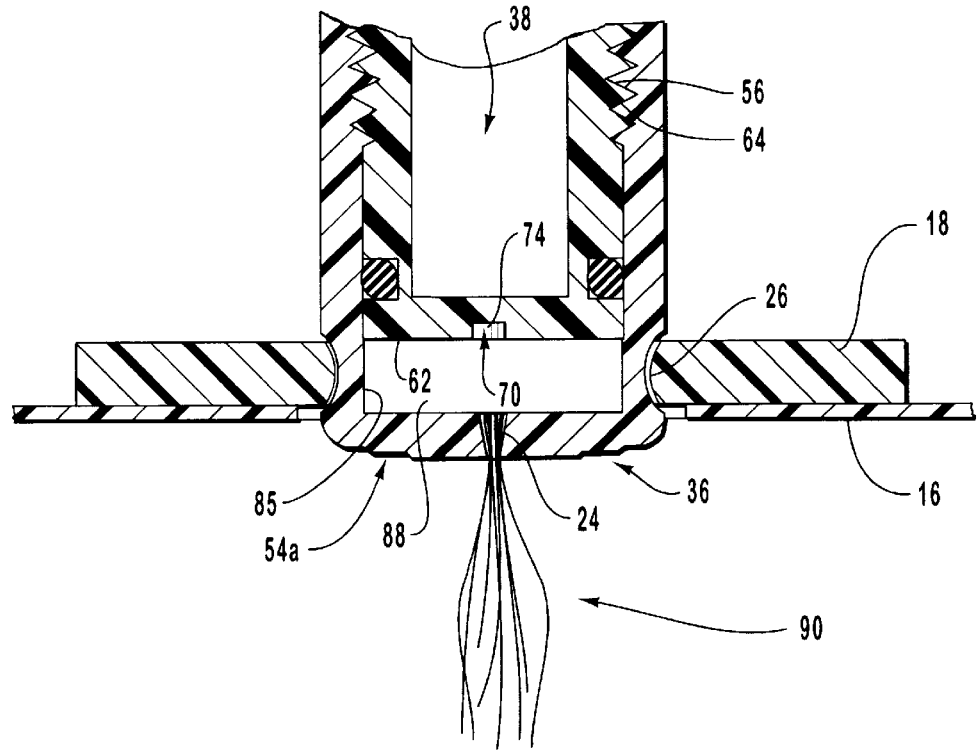
FIG. 5 is a cross-sectional cut away view as in FIG. 4 with the entrance tube moved away from the exit tube, which creates a focused spray pattern flowing from the exit hole.

Face 54 of fluid exit tube 50, as depicted in FIGS. 1 and 2, is substantially planar, which assists in preventing the risk of puncture wounds in the event face 54 is placed directly against the patient's body. Face 54a of exit tube 50, as depicted in FIGS. 4 and 5, also is substantially planar, although it is slightly tiered, as shown. The exterior surface of fluid exit tube 50 (FIG. 2) has longitudinal grooves 58 therein for providing a gripping surface when entrance tube 48 is selectively threaded into exit tube 50.

Fluid entrance tube 48 comprises a hollow cylindrical shaped member having a proximal opening 60 at an entrance end 34 thereof and a distal face 62 at an opposing end. Entrance tube 48 includes an external male threaded portion 64 located between distal face 62 and proximal opening 60 thereof. Entrance tube male threads 64 mate with female threads 56 on exit tube 50 such that entrance tube 48 moves longitudinally with respect to exit tube 50 when tubes 48, 50 are rotated relative to each other. This movement selectively positions distal face 62 of entrance tube 48 with respect to distal face 54 of exit tube 50.

Figure 3:
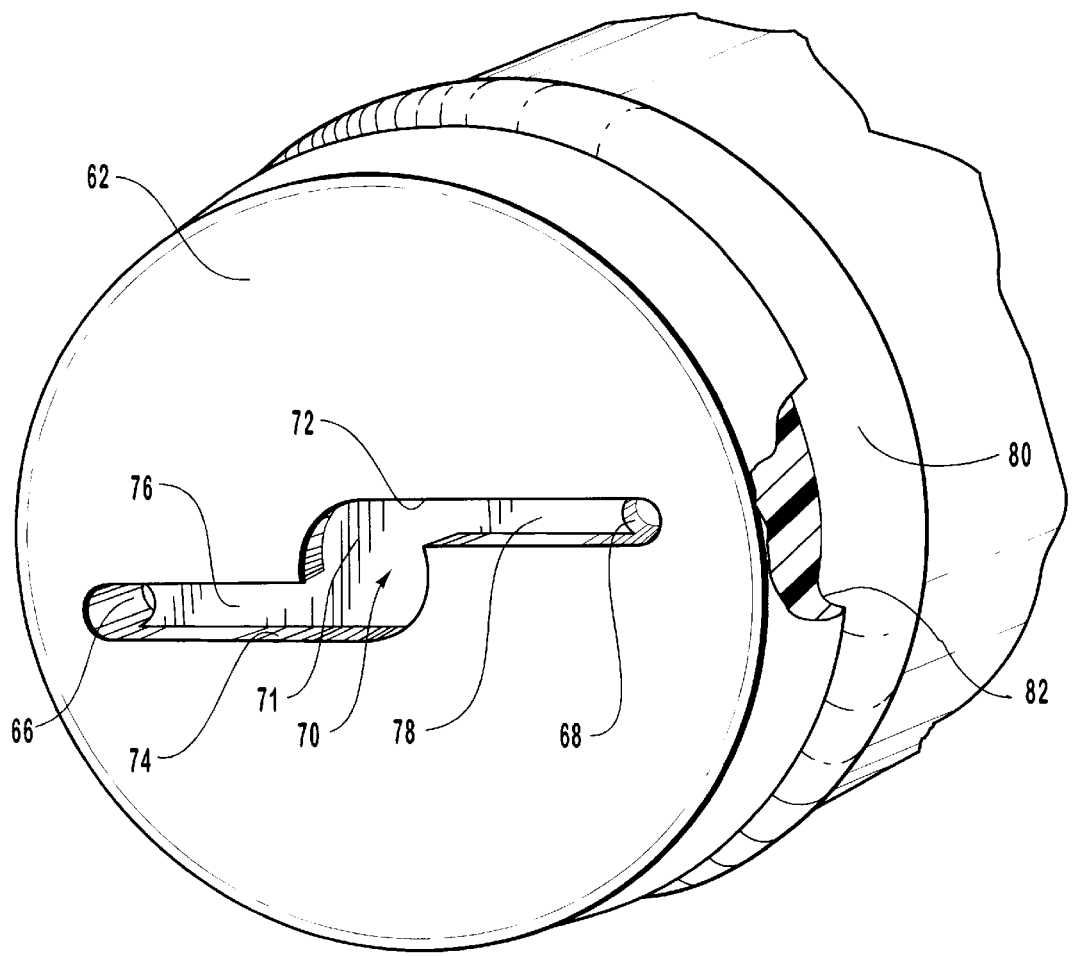
FIG. 3 is a cut-away view of an entrance tube of the irrigating system shown in FIG. 1.

With reference now to FIG. 3, distal face 62 of entrance tube 48 has at least one and preferably two exit holes 66, 68 therein. First and second exit holes 66, 68 are in fluid communication with a fluid collection groove 70 within face 62. Fluid collection groove 70 extends between upper and lower internal walls 72, 74 of face 62. Groove 70 comprises (i) a side channel 76 which extends from hole 66; (ii) another side channel 78 which extends from hole 68; and (iii) a central slot 71, with channels 76, 78 joining in central slot 71. Groove 70 thus interconnects holes 66, 68. FIG. 3 also demonstrates a fluid sealing O-ring 80 within an annular groove 82 in the exterior surface of entrance tube 48.

With reference now to FIGS. 4 and 5, fluid flow conduit 38 provides fluid communication between fluid entrance end 34 and fluid exit end 36 of adaptor 30. When distal face 62 of entrance tube 48 is located adjacent an inner surface of distal face 54a of exit tube 50, as shown in FIG. 4, fluid flow conduit 38 is defined by opening 60 of entrance tube 48, interior surface 84 of entrance tube 48, exit holes 66, 68, groove 70 and exit hole 24 in exit tube 50. When tubes 48, 50 are moved apart, as shown in FIG. 5, conduit 38 is further defined by the interior surface 85 of exit tube 50.

Slot 71 is located adjacent exit hole 24 of exit tube 50 when distal face 62 of entrance tube 48 is disposed adjacent distal face 54a of exit tube 50. In this relationship, fluid 86 flowing through tubes exit holes 66, 68 flows through channels 76, 78, into slot 71, creating a swirling motion, then flows out of exit hole 24, thereby creating a widely diffused mist, as shown in FIG. 4.

When faces 54a, 62 of respective tubes 50, 48 are separated, as shown in FIG. 5, the swirling motion created within slot 71 does not exist. Instead, a wall of fluid is formed in the cavity 88 between faces 54a, 62 with hole 24 as the sole fluid flow path to the environment. Thus, fluid 90 is expelled in a more concentrated or focused spray. The configuration of adaptor 30 thus enables the practitioner to selectively transmit fluid through adaptor 30 as one of (i) a widely diffused mist (see FIG. 4); (ii) a focused spray (see FIG. 5), or any number of spray patterns therebetween (not shown).

Sheet member 16 and hub 18 are both initially substantially planar, i.e., flat when resting on a planar surface. Thus, shield 14 is substantially planar when resting on a planar surface. In a preferred embodiment, adaptor 30 and hub 18 are configured to be coupled such that fluid exit end 36 of fluid delivery system 12 does not extend significantly beyond the plane defined by shield 14. This aids in reducing or eliminating the risk of puncture or irritation of the wound area. However, so long as face 54 of adaptor 30 is substantially planar itself, it may extend beyond the plane of hub 18. The important thing is to reduce the likelihood of a blunt or pointed member from puncturing, scraping, lacerating, or otherwise further irritating the wound area.

Figure 6:
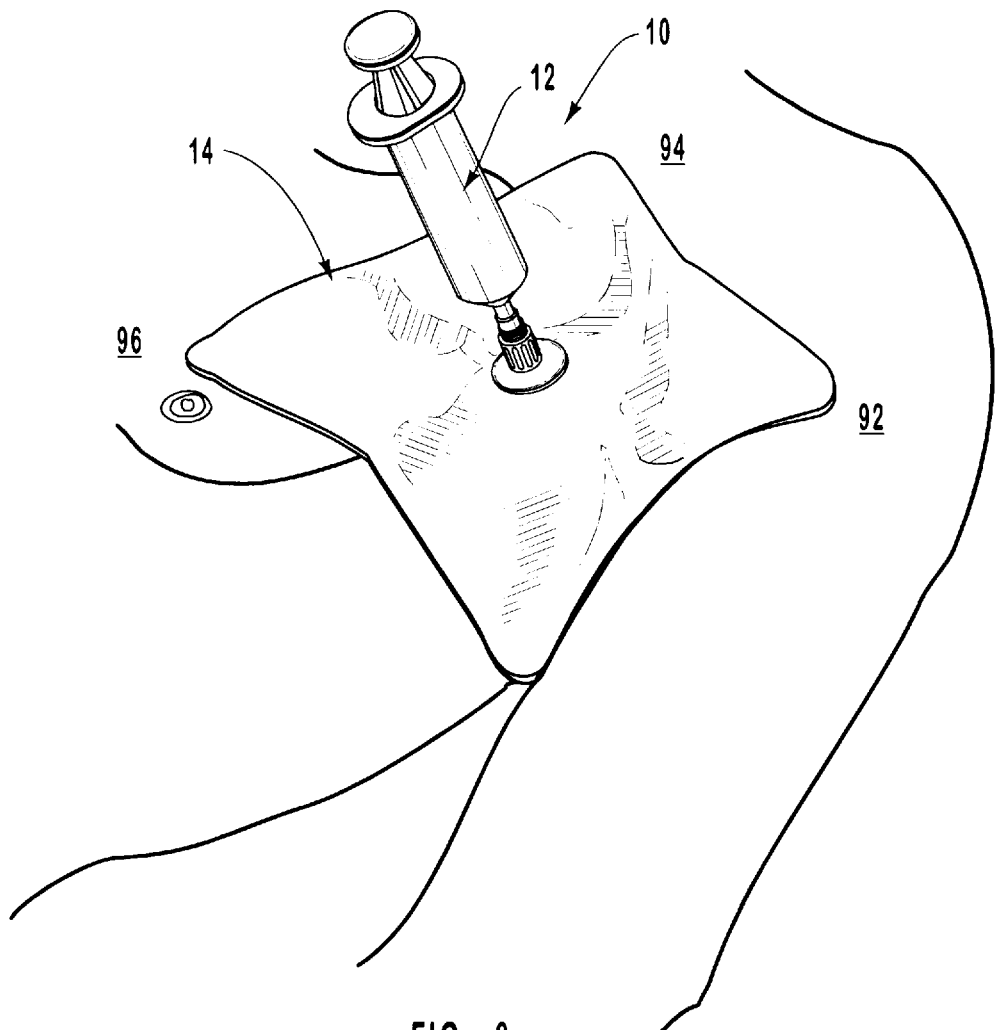
FIG. 6 is a view demonstrating the conformability of the flexible irrigation shield shown in FIG. 1. As shown, the shield conforms to an awkward, uneven area of the human body, namely the axial area, during irrigation of a wound on the patient's chest, shoulder or arm.

With reference now to FIG. 6, substantially flexible shield 14 is shown as preventing splashback of irrigation fluid provided to the body region located adjacent to a patient's axial area. As shown, different portions of shield 14 are draped over on the patient's arm 92, neck and shoulder region 94, chest region 96, and in a folding manner into the crevice between the arm and chest region. Each of the corners of substantially square, draping shield 14 conforms to its respective area of the body, despite the fact that each of the different bodily areas has divergent curvature and shape. Flexible, conformable shield 14 thus prevents fluid dispelled through fluid delivery system 12 from splashing back onto the practitioner despite possible awkward, uneven, curvatious nature of the body in this particular region and in a variety of other regions of the body. Of course, shield 14 also works well when treating flatter regions of the body, such as a stomach or chest. In addition, shield 14 may be rigid and still provide good protection when treating most, if not all, bodily areas. Flexibility is merely a preferred embodiment.

Another advantage resulting from the conformability of shield 14 is the ability to drape the peripheral portion of shield 14 directly against a patient's body, then irrigate the wound maintaining exit hole 24 slightly above the wound. Draped shield 14 prevents splashback from traveling outward because shield 14 is placed directly against the skin. Thus, draped shield 14 confines splashback to a small area adjacent the wound which is covered by shield 14.

Figure 7:
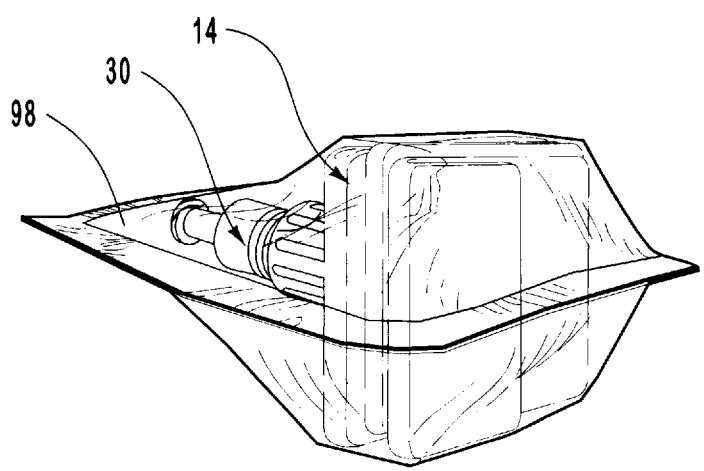
FIG. 7 is a view of the adaptor and flexible shield of the irrigating system shown in FIG. 1 with the shield shown in a folded, compact, storage position, and with the adaptor and shield enclosed in a sterile package.

As shown in FIG. 7, despite the large area of the body covered in FIG. 6, flexible, conformable shield 14 folds into a neat, compact unit for convenient storage and transport. A packaging material 98 may be disposed around the coupled shield 14 and adaptor 30 to retain the system in the folded, sterile condition. Adaptor 30 and shield 14 form a convenient, advantageous system for irrigating a wound with wound irrigation fluid from fluid source 28 and for preventing substantial splashback of the wound irrigation fluid. By unwrapping packaging material 98 then coupling adaptor 30 to a fluid source 28, the practitioner can readily and conveniently irrigate a wound. It will readily be appreciated, however, that adaptor 30 and shield 14 may be packaged separately from each other before use.

Figure 8:
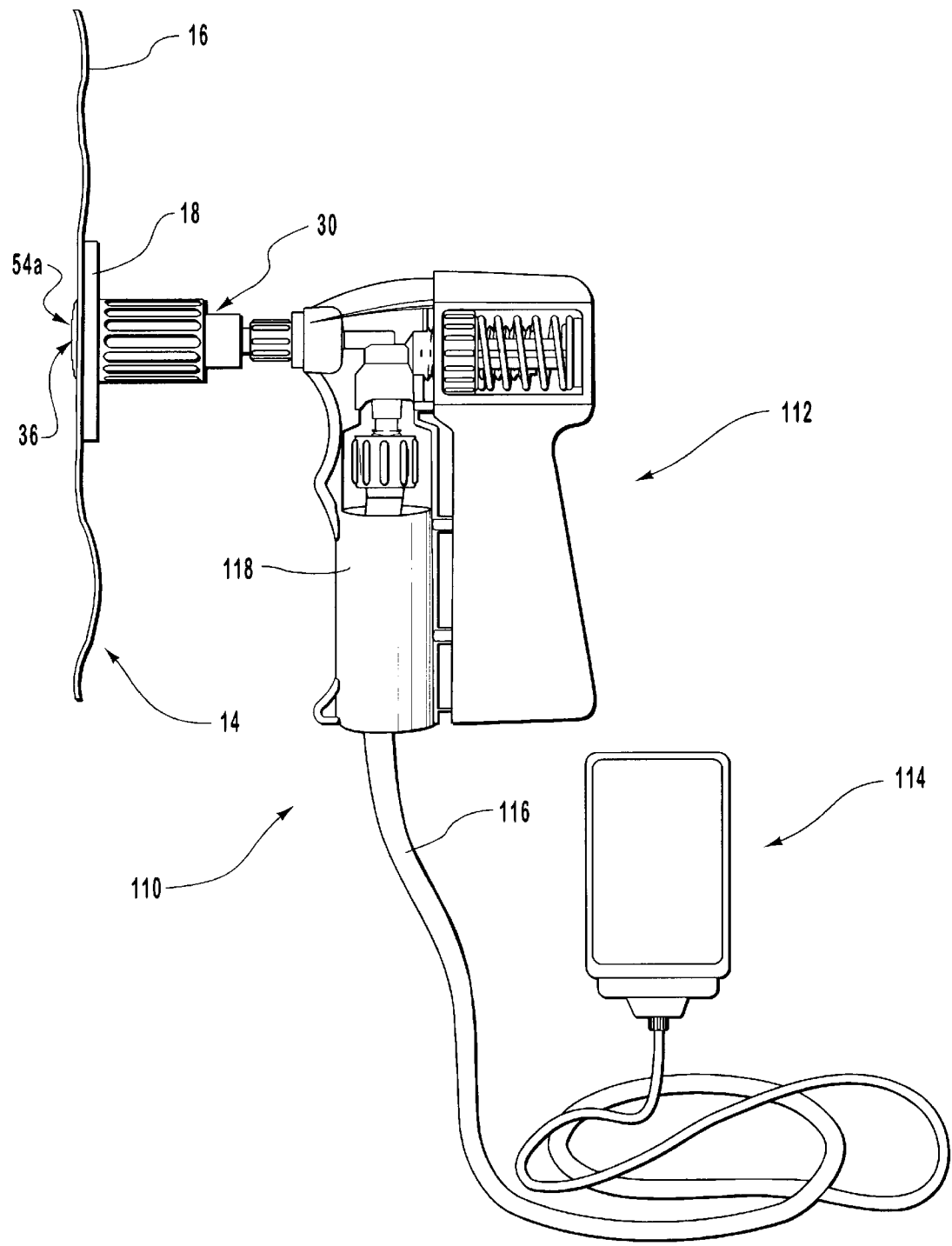
FIG. 8 is a view of another irrigating system of the present invention demonstrating an alternative fluid source.

FIG. 8 demonstrates another embodiment of an irrigating system 110 of the present invention. System 110 features shield 14, adaptor 30, and fluid source 112 removably coupled to adaptor 30. Fluid source 112 comprises a (i) fluid reservoir 114, such as a fluid bag, and (ii) means for directing fluid from reservoir 114 to adaptor 30, such as tube 116 and a pumping system 118 coupled to tube 116. A preferred example of fluid source 112 is described in detail in U.S. patent application Ser. No. 08/950,272 filed on Oct. 14, 1997 and entitled "One-Hand Pulse Pump," which, for purposes of disclosure, is incorporated herein in its entirety by specific reference. As shown in FIG. 8, fluid exit end 36 does not extend significantly beyond the plane defined by flexible shield 14. Instead, end 36 of exit tube 50 is located substantially within the plane defined by shield 14.

Figure 9:
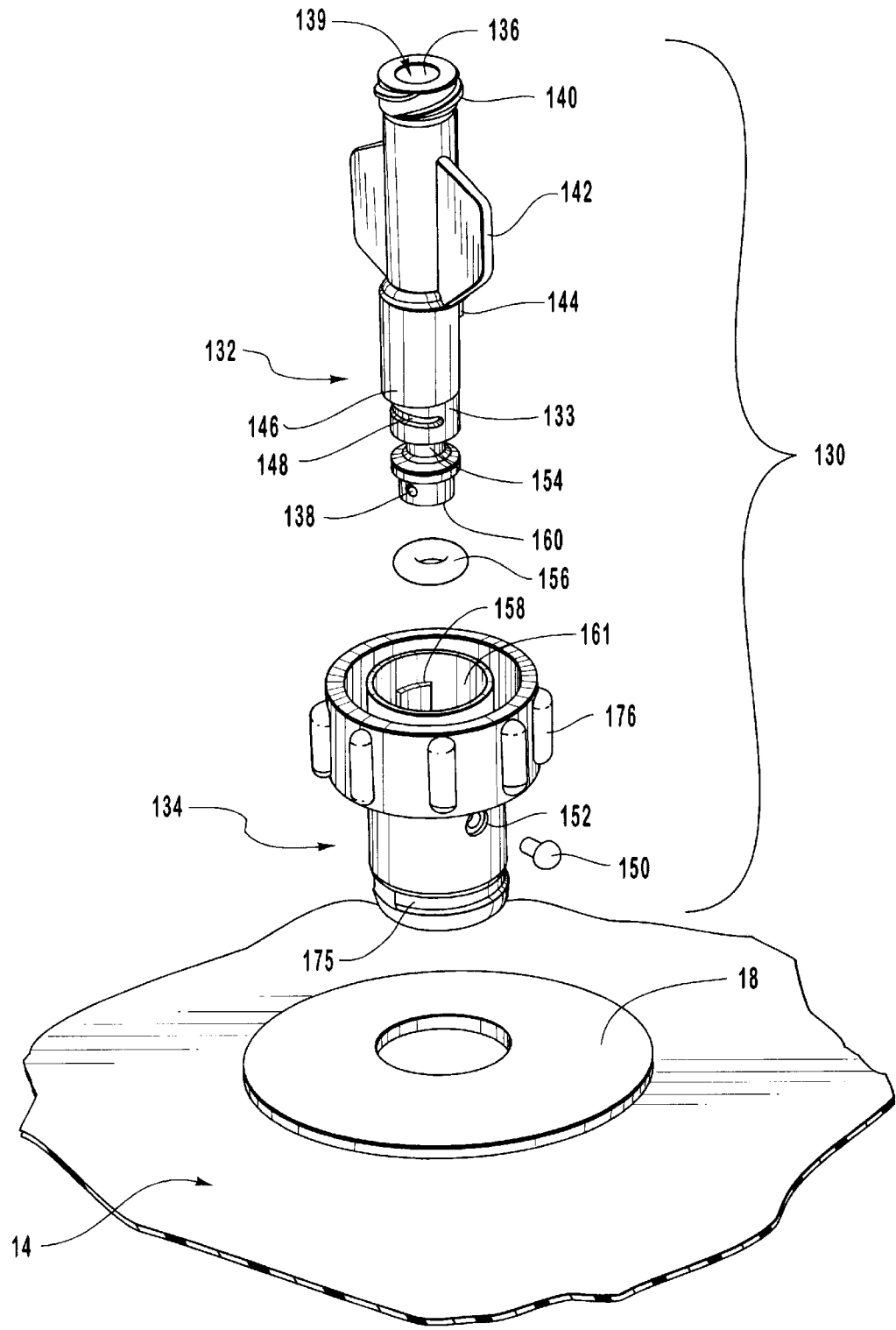
FIG. 9 is a view of an alternative adaptor of the present invention, demonstrating an alternative adaptor of the present invention.

With reference now to FIG. 9, another embodiment of an adaptor 130 of the present invention is shown in an exploded view. Adaptor 130 comprises an entrance tube 132 and an exit tube 134. Entrance tube 132 has a main body 133 having a proximal opening 136, first and second distal openings 138 on opposing sides of body 133, and a fluid pathway 139 extending between openings 138 and opening 136 for fluid to flow therethrough. As shown, entrance tube 132 includes a female Luer lock component 140 or other means for coupling a fluid source to entrance tube 132. Entrance tube 132 further includes wings 142 for selectively rotating entrance tube 132 into exit tube 134.

In order to selectively, removably couple entrance and exit tubes 132, 134, entrance tube 132 includes a groove 148 in main body 133 extending along at least a portion of the body 133 of entrance tube 132, groove 148 being angled with respect to an axis perpendicular to the longitudinal axis of entrance tube 132. Groove 148 receives a pin 150 which fits through an aperture 152 in exit tube 134. Because of the angled nature of groove 148, when tubes 132, 134 are rotated relative to each other, tubes 132, 134 move longitudinally relative to each other.

Main body 133 further includes an annular groove 154 which selectively receives O-ring 156 to thereby prevent fluid from flowing from openings 138 to proximal opening 158 of exit tube 134. In one embodiment, the face 160 of entrance tube 132 is closed, meaning that there is no hole through face 160, but, rather, fluid emanates only from distal openings 138 on opposing sides of body 133.

Figure 10:
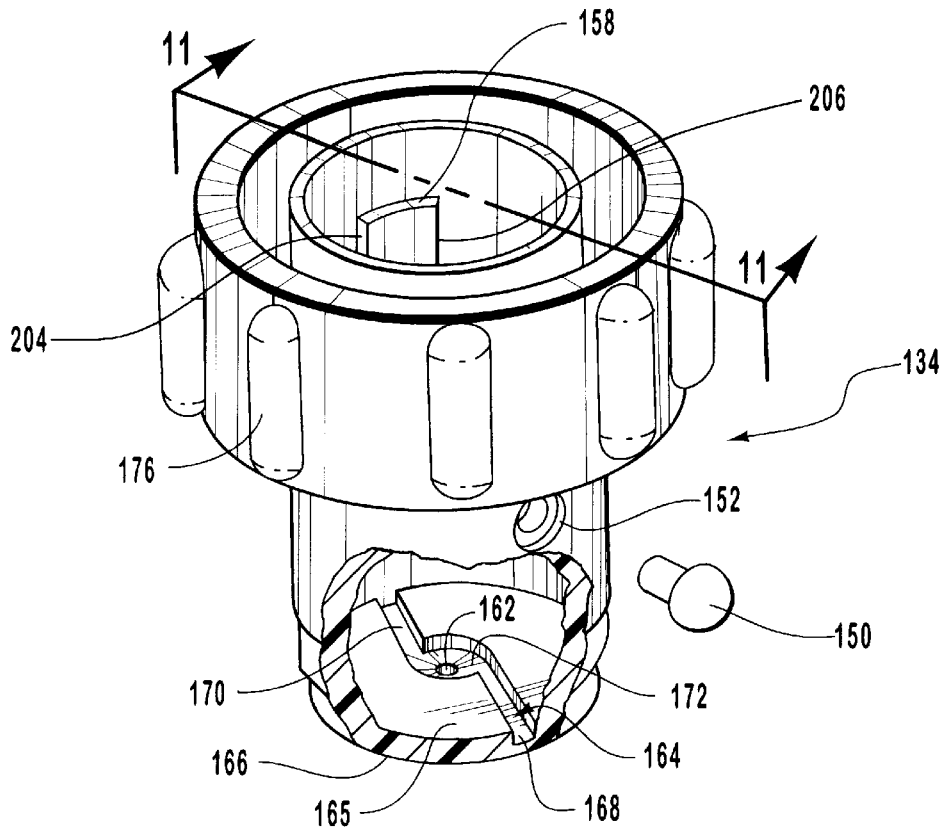
FIG. 10 is a cut-away view of a fluid exit tube of the adaptor shown in FIG. 9.
Figure 11:
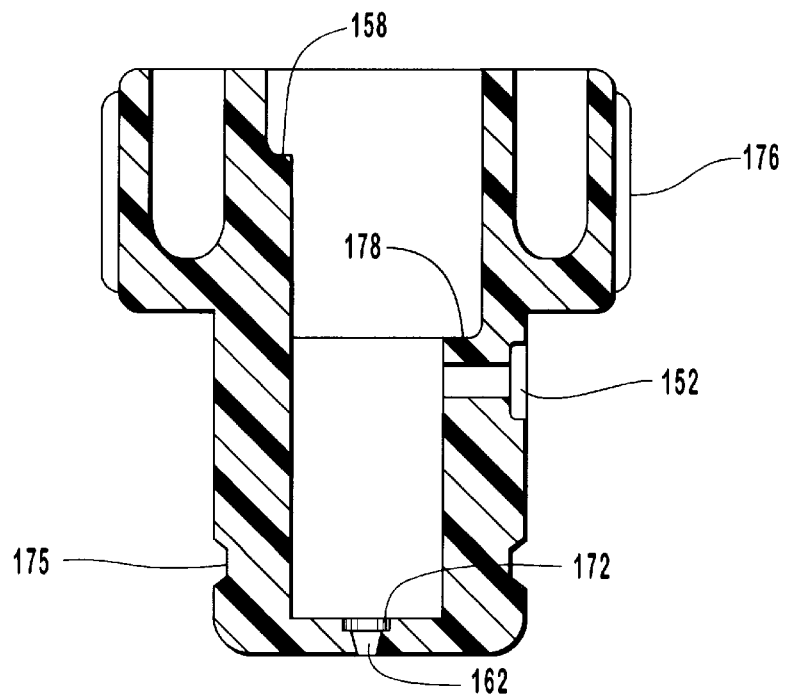
FIG. 11 is a cross sectional view of the fluid exit tube shown in FIG. 10.

Exit tube 134 includes proximal opening 161 and a distal exit opening 162 shown in FIGS. 10 and 11. Exit tube 134 also includes a fluid collection groove 164 in the interior portion of the face 166 thereof. Groove 164 comprises a first channel 168, a second channel 170 and a central slot 172 adjoining first and second channels 168, 170. Distal exit opening 162 extends through groove 164. In one embodiment, opening 162 is conical in shape.

As distal face 160 of entrance tube 132 is placed against interior portion 165 of face 166 of exit tube 134, fluid flowing from openings 138 flows into first and second channels 168, 170 and then flows into central slot 172 creating a swirling motion which thereby creates a widely diffused mist emanating from opening 162. However, when distal face 160 is extended away from interior surface 165 of face 166, a wall of irrigation fluid is formed between face 160 of entrance tube 132 and opening 162 causing the fluid sprayed to be wider or narrower as desired.

With reference now to FIG. 11, internal ridges 158 and 178 in exit tube 134 are shown. In one embodiment, these internal ridges 158, 178 have mating surfaces for external shoulders 144, 146 of entrance tube 132 and shoulders 144, 146 of entrance tube 132 abut ridges 158, 178 when the maximum distance of movement of groove 148 with respect to pin 150 has been reached as entrance tube 132 is rotated into exit tube 134.

Exit tube 134 further includes a groove 175, such as an annular groove, in the exterior surface thereof for selectively receiving shield 14. Gripping bumps 176 are shown on the exterior surface of exit tube 134. Thus, a number of different embodiments of adaptors for the present invention are envisioned. In other embodiments of a multi-piece adaptor, the adaptor pieces are press fit together or selectively snap into each other.

Figure 12:
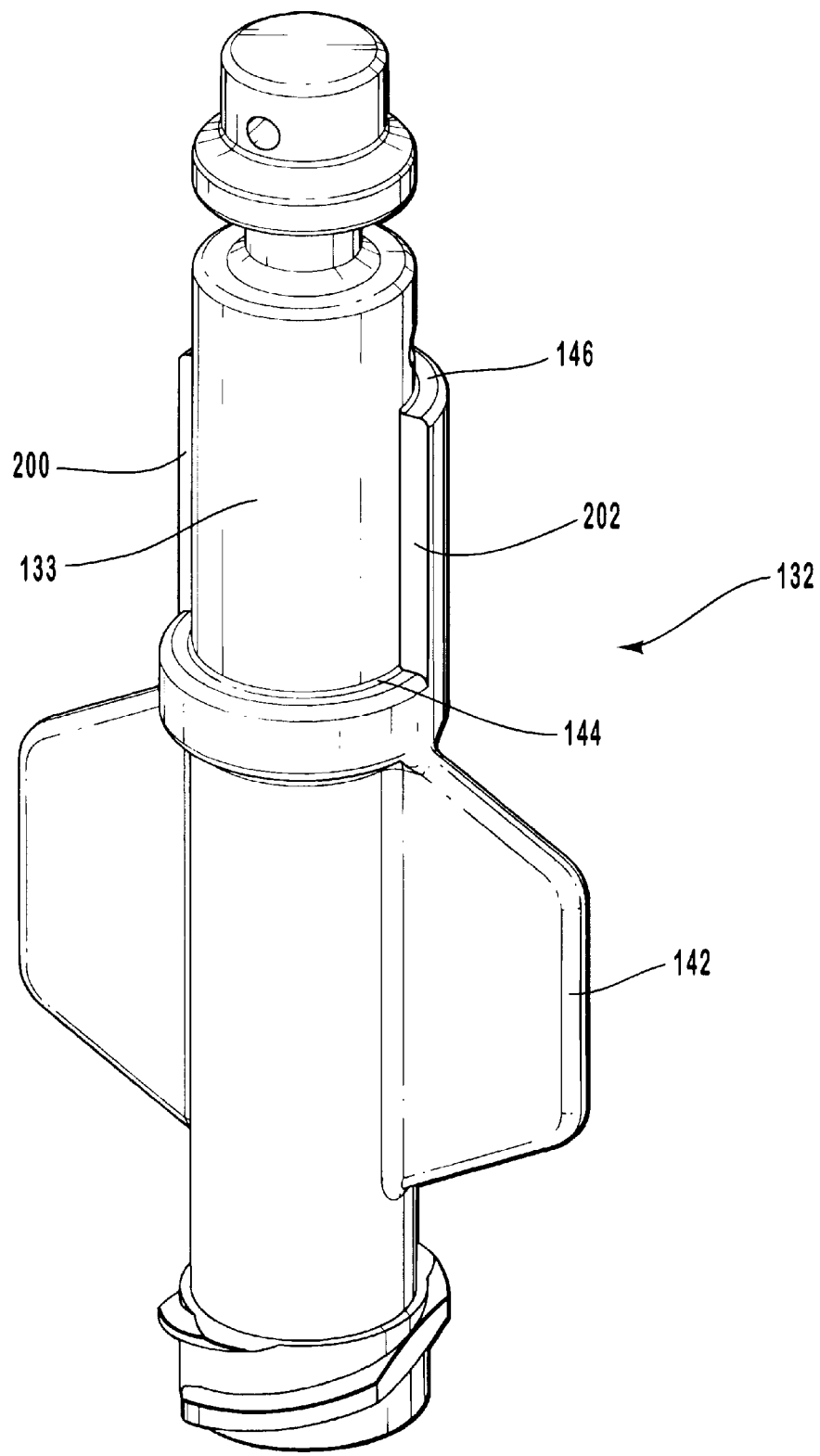
FIG. 12 demonstrates an entrance tube of the adaptor of FIG. 9 shown from an alternative view.

FIG. 12 demonstrates an opposing, inverted view of entrance tube 132 from that of FIG. 9. Sides 200, 202 of shoulder 146 abut respective, opposing sides 204, 206 of ridge 158, serving as stops as entrance tube 132 is rotated within exit tube 134.

Adaptors 30 and 130 are particularly useful when a practitioner desires to retrofit shield 14 onto an existing syringe or other fluid source. However, it will also be appreciated that each of the fluid sources mentioned above, such as a syringe, hand pump, squeeze bottle, etc. may independently constitute a fluid delivery system for applying irrigation fluid to a wound area without the use of a separate adaptor, such as adaptor 30 or adaptor 130. Thus, one embodiment of an irrigating system of the present invention comprises (i) a fluid delivery system for applying irrigation fluid to a wound area, such as syringe 28, a hand pump or a squeeze bottle, fluid bag, pressurized tank, or other fluid delivery system; and (ii) shield 14 coupled (permanently or removably) to the syringe 28, hand pump, squeeze bottle, fluid bag, tank, or other system, such as by having a portion of the syringe 28 or hand pump, for example, disposed through aperture 20 of shield 14 as discussed above. A syringe or other fluid delivery system may have a groove therein, for example, for reception of shield 14.

In conclusion, the wound irrigation systems of the present invention can cover a desired area during irrigation, yet the shield can be folded compactly for transport and storage. System 10 can also feature spray pattern adjustability and reduced risk of patient puncture. Shield 14 preferably features flexibility, removability, rotation, and disposability. A variety of different fluid sources and adaptors may be coupled, preferably removably, to shield 14.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system for irrigating a wound area with wound irrigation fluid while preventing substantial splashback of the wound irrigation fluid, the system comprising:

a fluid source for providing wound irrigation fluid;

means for transmitting fluid from the fluid source to the wound area; and a completely flexible, non-rigid wound irrigation shield that drapes over a wound area, and which is configured to prevent substantial splashback of the irrigation fluid upon irrigation of a wound area.

2. An irrigating system as recited in claim 1, wherein the flexible shield is affixed to the means for transmitting fluid.

3. An irrigating system as recited in claim 1, wherein the flexible shield is removably coupled to the means for transmitting fluid.

4. An irrigating system as recited in claim 1, wherein the shield is substantially planar when resting on a planar surface and wherein the means for transmitting fluid does not extend significantly beyond the plane defined by the shield.

5. An irrigating system as recited in claim 1, wherein the shield comprises flexible sheet means for preventing substantial splashback of a fluid applied to a wound area; and hub means for coupling the flexible sheet means to the means for transmitting fluid.

6. An irrigating system as recited in claim 5, wherein the hub means is configured to receive the means for transmitting fluid therethrough.

7. An irrigating system as recited in claim 5, wherein the flexible sheet means comprises a substantially flexible sheet member and the hub means comprises a substantially rigid disk coupled to the sheet member.

8. An irrigating system as recited in claim 1, wherein the fluid source comprises a reservoir and means for pumping fluid from the reservoir to the means for transmitting fluid.

9. An irrigating system as recited in claim 1, wherein the fluid source comprises a syringe.

10. An irrigating system as recited in claim 1, wherein the means for transmitting fluid comprises an adaptor for coupling the fluid source to the wound irrigation shield, the adaptor comprising:

a main body having a fluid entrance end, a fluid exit end, and a fluid flow conduit providing fluid communication between the fluid entrance and exit ends;

means for coupling the fluid entrance end of the main body to the fluid source; and means for coupling the fluid exit end of the main body to the wound irrigation shield.

11. An irrigating system as recited in claim 1, wherein the shield is configured to rotate relative to the means for transmitting fluid from the fluid source to the wound area.

12. A system for irrigating a wound area with wound irrigation fluid and for preventing substantial splashback of the wound irrigation fluid, the system comprising:

fluid delivery means for delivering wound irrigation fluid; and a completely flexible, non-rigid wound irrigation shield that drapes over a wound area, and which is configured to be coupled to the fluid delivery means such that the irrigation shield prevents substantial splashback of the irrigation fluid upon irrigation of a wound area.

13. An irrigating system as recited in claim 12, wherein the shield is configured to be removably coupled to the fluid delivery means.

14. An irrigating system as recited in claim 12, wherein a fluid exit hole of the fluid delivery means does not extend significantly beyond a plane defined by the shield.

15. An irrigating system as recited in claim 14, wherein the fluid delivery means has a face located substantially within the plane defined by the shield.

16. An irrigating system as recited in claim 15, wherein the face is substantially planar.

17. An irrigating system as recited in claim 12, wherein an exterior surface of the fluid delivery means has a groove therein for removably receiving a hub of the wound irrigation shield.

18. An irrigating system as recited in claim 17, wherein the hub has an aperture sized and configured such that the hub selectively forms a snap fit engagement within the groove.

19. An irrigating system as recited in claim 12, wherein the shield is capable of being folded into a compact position.

20. A system for irrigating a wound area with wound irrigation fluid and for preventing substantial splashback of the wound irrigation fluid, the system comprising:
   fluid delivery means for delivering wound irrigation fluid; and
   a wound irrigation shield configured to be removably coupled to the fluid delivery means such that the shield prevents substantial splashback of the irrigation fluid upon irrigation of a wound area, the shield comprising:
      a completely flexible non-rigid sheet which drapes over a wound area, and which is capable of being folded into a compact position; and
      a substantially rigid hub coupled to the flexible sheet and configured to mate with a corresponding structure of the fluid delivery means.

21. A system as recited in claim 20, wherein the hub is configured to snap fit onto the fluid delivery means and to selectively rotate relative to the fluid delivery means.

22. A system for irrigating a wound with wound area irrigation fluid while preventing substantial splashback of the wound irrigation fluid, the system comprising:
   a fluid source for providing wound irrigation fluid;
   a flexible wound irrigation shield configured such that the shield prevents substantial splashback of the irrigation fluid upon irrigation of a wound area; and
   an adaptor for coupling a fluid source to a wound irrigation shield, the adaptor comprising:
      a main body having a fluid entrance end, a fluid exit end, and a fluid flow conduit providing fluid communication between the fluid entrance and exit ends;
      means for coupling the fluid entrance end of the main body to a fluid source;
      means for coupling the fluid exit end of the main body to the wound irrigation shield, and
      wherein the adaptor is adjustable, thereby enabling the user to selectively adjust the spray pattern of fluid flowing out of the exit end of the adaptor.

* * * * *

UNITED STATES PATENT AND TRADEMARK OFFICE
CERTIFICATE OF CORRECTION

PATENT NO. : 6,050,981
DATED : April 18, 2000
INVENTOR(S) : Fred P. Lampropoulos, Brent E. Mabey, Arlin Dale Nelson, Gregory R. McArthur, Jerrold L. Foote It is certified that error appears in the above-identified patent and that said Letters Patent is hereby corrected as shown below:

Cover Page, in the Abstract, ln. 4: after "delivery" change "device to --means--

Cover Page, in the Abstract, ln. 13: after "delivery" change "device to --means--

Cover Page, in the Abstract, ln. 15: after "(ii)" change "an adaptor" to --means--

Cover Page, in the Abstract, ln. 16: after "wound" insert --such as an adaptor--

Col. 4, ln. 28: after "now" and before "described" insert --be--

Col. 6, ln. 28: after "in the" insert --art.--

Col. 8, ln. 13: after "which" change "couple" to --couples--

Col. 9, ln. 29: after "corners of" and before "substantially" insert --the--

Signed and Sealed this

Twenty-fourth Day of April, 2001

Attest:

NICHOLAS P. GODICI

Attesting Officer

Acting Director of the United States Patent and Trademark Office